United States Patent [19]

Kordes

[11] Plant 4,798

[45] Jan. 19, 1982

[54] ROSE PLANT—JP 435

[75] Inventor: Reimer Kordes, Sparrieshoop, Fed. Rep. of Germany

[73] Assignee: Jackson & Perkins Company, Medford, Oreg.

[21] Appl. No.: 175,491

[22] Filed: Aug. 5, 1980

[51] Int. Cl.[3] ..... A01H 5/00

[52] U.S. Cl. ..... Plt./11

[58] Field of Search ..... Plt./11

*Primary Examiner*—Robert E. Bagwill

*Attorney, Agent, or Firm*—Klarquist, Sparkman, Campbell, Leigh, Whinston & Dellett

[57] ABSTRACT

A hybrid tea rose variety having orange and yellow flowers on a medium size bush.

1 Drawing Figure

This present invention relates to a new and distinct variety of rose plant of the hybrid tea class which was originated by me by crossing the variety Ludwigshafen am Rhein with pollen of the variety, Feuerzauber.

The primary objective of this breeding was to produce a new rose variety of the hybrid tea class, producing freely large blooms of orange and yellow colors, in a bicolor effect. This objective was substantially achieved along with other desirable improvements as evidenced by the following unique combination of characteristics which are outstanding in the new variety and which distinguish it from its parents as well as from all other varieties of which I am aware:

1. A medium size hybrid tea bush.
2. Flowers of generally orange color on upper side of petals, yellow on lower side.
3. Short peduncles, having both small prickles and stipitate glands.
4. Little or no fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Royal Horticultural Society Colour Chart except where ordinary dictionary significance of color is indicated.

Parentage:

*Seed parent.*—Ludwigshafen am Rhein.

*Pollen parent.*—Feuerzauber.

Classification:

*Botanical.*—Rosa hybrid.

*Commercial.*—Hybrid Tea.

FLOWER

Observations made from specimens grown outside at Irvine, Calif., in November, 1979.

Blooming habit: Continuous.

Bud:

*Size.*—1¼" to 1½" when petals start to unfurl.

*Form.*—Short, blunt top.

*Color.*—When sepals first divide, base color near RHS Yellow-Orange 21D overlaid over major portion of outside petals with a pigment near RHS Greyed Red 179A; when half blown, upper side of petals near RHS Orange-Red 33A with a distinctly defined area at base of petal of RHS Yellow 11A; lower side of petals mostly RHS Yellow 11C showing some coloration "bleeding" through of the pigment on the upper side, Orange-Red 33A.

*Sepals.*—Color: Outer surface near green, RHS 136C; three appendaged sepals heavily appendaged or foliated; two unappendaged sepals hairy edged.

*Receptacle.*—Color: between RHS Green 136C and 136D. Shape: funnel. Size: large. Surface: smooth.

*Peduncle.*—Length: short. Surface: prickly and glandular. Color: light green and bronzy. Strength: stiff, erect.

*Opening.*—Very little curling back of petal tips as flower opens.

Bloom:

*Size.*—Large. Average open size 5".

*Borne.*—Singly.

*Stems.*—Medium, strong.

*Form.*—When first open, high centered. Permanence: outer petal edges slightly curled.

*Petalage.*—Number of petals under normal conditions: 25.

*Color.*—Center of flower: upper side of petals near 33B, RHS Orange-Red. Reverse side of petals near RHS Yellow 11C. Base of petals RHS Yellow 11A. General tonality from a distance Orange-Red 33A.

*Variegations.*—Occasional midrib streak of yellow.

*Discoloration.*—General tonality at end of first day, RHS Orange-Red 33A; third day, RHS Orange-Red 33B, gradually changing to 33C.

*Fragrance.*—Slight to none.

Petals:

*Texture.*—Thick.

*Shape.*—Broad, oval.

*Form.*—Tips slightly recurved.

*Arrangement.*—Irregular. Petaloids in center, few.

*Persistence.*—Drop off cleanly.

*Lastingness.*—On the plant, fair. As cut flower, fair.

Reproductive parts:

*Anthers.*—Medium. Color: yellow. Arrangement: regular around styles.

*Filaments.*—Color: basal portion Yellow 12B changing to Yellow-Orange 22B toward distal portion.

*Pollen.*—Lemon yellow.

*Styles.*—Color: reddish.

*Stigmas.*—Color: yellow.

PLANT

Form: Bush.

Growth: Very vigorous. Plant grows to approximately 4½ feet with normal cultural practices at Irvine, Calif.

Foliage: Number of leaflets on normal mid-stem leaves: 5.

*Size.*—Medium.

*Quantity.*—Normal.

*Color.*—New foliage: near Greyed-Purple 187B, changing upon unfolding to Green 131A. Old foliage: near Green 131A.

Leaflets:

*Shape.*—Oval pointed.

*Texture.*—Leathery.

*Edge.*—Serrated.

*Serration.*—Single, small.

*Petiole.*—Rachis. Color: reddish. Underside: few prickles.

*Stipules.*—Long, bearded.

*Disease resistance.*—Normally resistant to mildew, blackspot under normal growing conditions at Irvine, Calif.

Wood:

*New wood.*—Color: bronzy brown. Bark: smooth.

*Old wood.*—Color: green. Bark: smooth.

Prickles:

*Quantity.*—On mail stalks from base: ordinary. On laterals from stalk: ordinary.

*Form.*—Long base; long, hooked downward.

*Color when young.*—Brown.

*Position.*—Irregular.

Small prickles:

*Quantity.*—On main stalks, none. On laterals, none.

I claim:

1. A new and distinct variety of rose plant of the hybrid tea class, substantially as herein shown and described, characterized particularly as to novelty by the unique combination of its medium size (4½') bush, orange and yellow flowers, short peduncles having both glands and prickles and its very slight to non-existent fragrance.

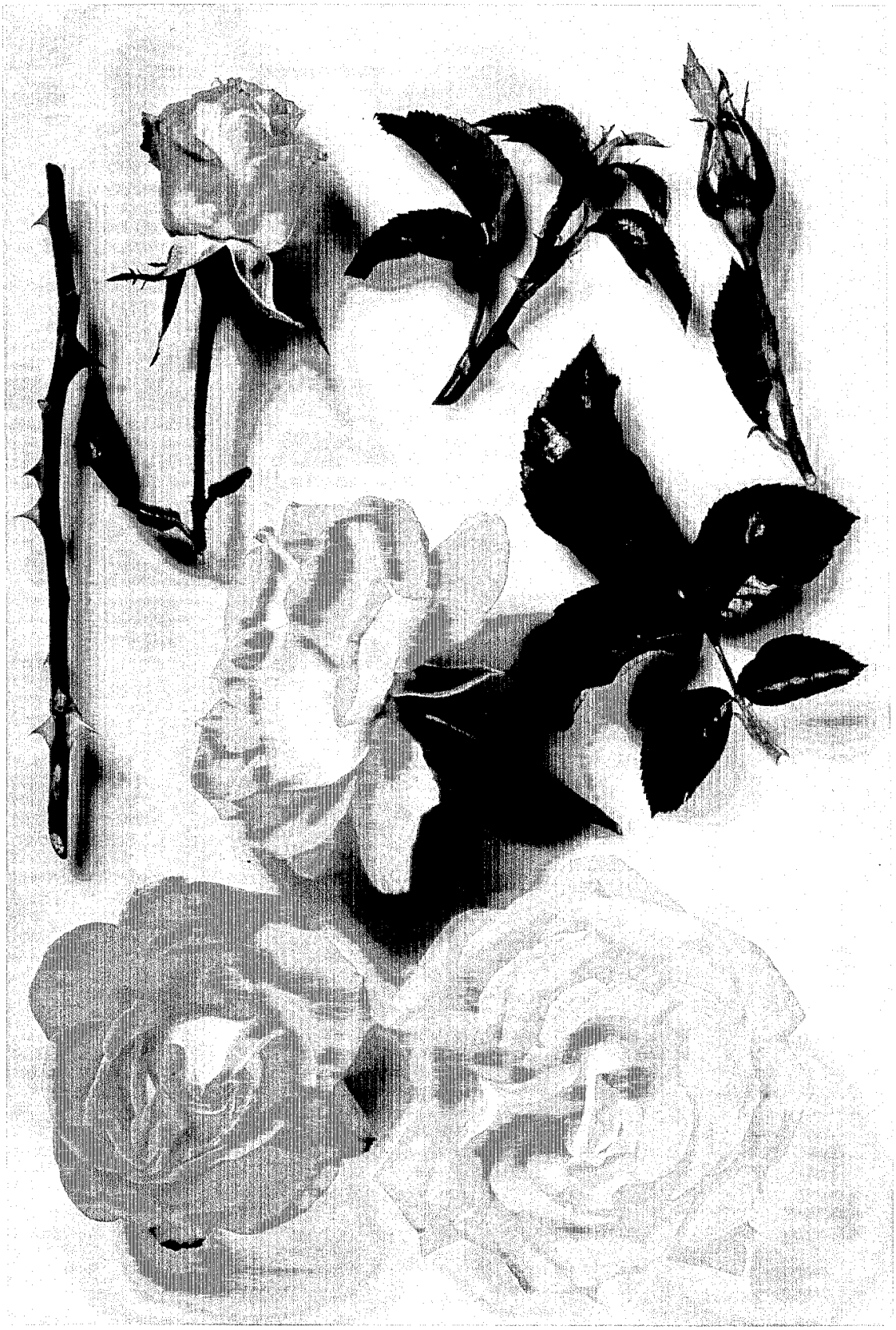

* * * * *